United States Patent [19]

Reardon

[11] Patent Number: 5,078,426
[45] Date of Patent: * Jan. 7, 1992

[54] FINGERPRINT RECORDING DEVICE

[76] Inventor: David C. Reardon, 50 Nottingham, Springfield, Ill. 62704

[*] Notice: The portion of the term of this patent subsequent to Jul. 24, 2007 has been disclaimed.

[21] Appl. No.: 548,384

[22] Filed: Jul. 3, 1990

Related U.S. Application Data

[63] Continuation-in-part of Ser. No. 352,888, May 17, 1989, Pat. No. 4,943,089.

[51] Int. Cl.$^5$ .............................................. B42D 15/00
[52] U.S. Cl. ........................................ 283/78; 283/68
[58] Field of Search .......................... 283/68, 69, 78; 281/15.1

[56] References Cited

U.S. PATENT DOCUMENTS

| | | | |
|---|---|---|---|
| 1,374,208 | 4/1921 | Jones | 283/78 |
| 1,543,747 | 6/1925 | Brey | 281/15.1 |
| 2,006,744 | 7/1935 | Pierce | 283/78 |
| 2,500,612 | 3/1950 | Krogh | 283/78 |
| 2,912,259 | 11/1959 | Young | 283/78 |
| 3,447,818 | 6/1969 | Pizzol | 283/68 |
| 3,467,055 | 9/1969 | Yonchar | 283/78 |
| 3,664,910 | 5/1972 | Hollie | 283/69 |
| 3,709,524 | 1/1973 | McKee et al. | 283/78 |
| 4,669,753 | 6/1987 | Land et al. | 283/78 |
| 4,706,600 | 11/1987 | Mason, Jr. et al. | 283/78 |
| 4,943,089 | 7/1990 | Reardon | 283/81 |

Primary Examiner—Frank T. Yost
Assistant Examiner—Hwei-Siu Payer

[57] ABSTRACT

A quick and clean method of recording fingerprints without inks, chemicals, or powders is disclosed. The invention is especially suited for incorporation into mass produced legal and financial documents, wherein a portion of a document is fabricated to include a protected area for the recording and preservation of a latent fingerprint. The fingerprint receptive area of the document is protected by a cover which removably adheres to the document. If the identity of a party signing the document is later questioned, the cover may be removed from the pad to expose the fingerprint for forensic processing or AFIS scanning.

8 Claims, 1 Drawing Sheet

FINGERPRINT RECORDING DEVICE

This application is a continuation-in-part of application Ser. No. 352,888, filed May 17, 1989, now U.S. Pat. No. 4,943,089.

BACKGROUND OF THE INVENTION

1. Field of the Invention

The present invention relates generally to an identification system comprising a device for obtaining and recording fingerprint data. More particularly, the invention relates to an improved fingerprint recording device on which a fingerprint can be imprinted and stored on a particular legal or business document for the purpose of affixing to the document a permanent record of evidence of the identity of the individual involved in the legal or financial transaction.

2. Cross-Reference to Related Applications

U.S. Pat. No. 4,943,089 to Reardon discloses a fingerprint pad which employs a reflective substrate material which enhances the fingerprint image and the use of a removable cover for ease of processing a questioned fingerprint. The present invention in part discloses and claims subject matter disclosed in U.S. Pat. No. 4,947,089 to Reardon.

3. Description of the Prior Art

In the past, financial and legal transactions have always been susceptible to fraud through misrepresentation of identity, forgery of signatures, and the counterfeiting of documents, such as traveller's checks. The use of fingerprints in conjunction with signatures, or in the place of signatures, would serve as a deterrent to fraud and provide evidence for the prosecution of criminals engaged in the above crimes. The taking of fingerprints, however, has previously been a time consuming and messy task involving inks, or in a few cases, a combination of special chemicals and chemically sensitized paper.

The first need which inventions in this field must address is the need for a clean method of taking fingerprints. This requires the elimination of any inks, chemicals, or powders which would make a person feel that the fingerprinting method has made their hands dirty. The second requirement is that the resulting device must be free of materials or techniques which are too expensive or complicated to manufacture using standard mass production techniques.

The present invention satisfies both of these requirements. In addition to providing a very clean alternative to inked fingerprints, it discloses a low-cost design which involves a minimal number of parts which can be easily incorporated into the mass production of transaction documents such as traveler's checks, credit card transaction slips, driver's applications, and tax returns, to name a few.

Various prior art fingerprint devices and the like, are well known and are to be found to be exemplary of the U.S. prior art. U.S. Pat. No. 2,500,612 to Krough discloses a device for placing fingerprints on documents. This invention includes the use of powder on the finger before the impression is made on a pad. U.S. Pat. No. 3,467,055 to Yonchar teaches of a device for preserving fingerprints on a document, which includes a complex series of folded strips and the use of a powdery substance.

The most notable example of the prior art is contained in U.S. Pat. No. 3,664,910 to Hollie. Hollie discloses a document identification system where a stamp-like patch comprised of a multiplicity of layers is adhesively attached to a document. To use Hollie's device, the user must first peel off and discard a protective backing sheet to expose an adhesive layer by which the patch is attached to the document. Then, to record the fingerprint, the person must lift a transparent cover sheet, then he must peel off an intermediary isolating liner which must be discarded, then he must impress a fingerprint onto the exposed layer of pressure-sensitive adhesive, and finally he must press the transparent cover sheet back down over the fingerprint image to lock-in and preserve the fingerprint image, whereby the cover becomes irremovably adhered to the pressure-sensitive adhesive. Though the fingerprint image recorded by Hollie's invention is not visible to the naked eye, it can be made visible with special wavelengths of light and photographed through the protective cover.

All of the fingerprint pads heretofore known suffer from a number of disadvantages, including the use of messy powders or chemicals, the use of expensive multiple layers, the requirement for disposable dividing layers which must be detached and thrown away, the use of irremovable covers which obstruct the processing of the fingerprint image, or other design features which preclude low-cost construction and mass production.

Furthermore, the prior art, as in the inventions of Hollie and U.S. Pat. No. 4,943,089 to Reardon, relies on the use of adhesives for affixing a fingerprint pad device to the document in question. In these devices, the fingerprint lies on a substrate material separated from the document by an adhesive. This common technique leaves open the possibility that fraud may be achieved by peeling the substrate material off of the document and attaching it to some other document which is fraudulent. The present invention prevents this avenue of fraud by eliminating the adhesive and substrate material and using the document itself as an integral and irremovable member of the fingerprint recording device.

These patents or known prior uses teach and disclose various types of fingerprint recording devices of various sorts and manufactures as well as methods of construction; but none of them, whether taken singly or in combination, disclose the specific details of the present invention.

The present invention is an improvement over the prior art in that it provides a construction which does not soil the user's hand with any inks, powders, or chemicals; it produces a fingerprint image which is visible to the naked eye; it does not require the peeling and discarding of intermediate waste materials; and it provides for a removable cover which allows for unobstructed processing of the fingerprint image. In addition, the invention eliminates the use of excessive layers and components which would increase cost and otherwise complicate the mass production of documents incorporating this device.

SUMMARY OF INVENTION

The objects, advantages and features of the present invention are:

(a) to provide a fingerprint recording device which is simple to operate, convenient to use, and can be inexpensively incorporated onto mass produced documents, such as are generally used for financial, business, or legal transactions;

(b) to provide a fingerprint recording device which incorporates into the device a portion of the document itself as an irremovable component of the fingerprint carrying substrate;

(c) to provide a fingerprint recording device which cannot be switched to another document without causing irreparable damage to the fingerprint image or the pad itself so as to provide unmistakable evidence of tampering.

(d) to provide a fingerprint recording device which has a protective cover which will preserve the fingerprint and which can be easily lifted for application of the fingerprint and later removed for unobstructed processing of the fingerprint;

(e) to provide a fingerprint recording device which can be customized to suit the application's needs with such optional features as:
 1) an adhesive-like fingerprinting medium which improves the capture and retention of the latent fingerprint;
 2) the use of a reflective surface on the document which enhances the visibility of the fingerprint image;
and yet provide for these options without violating the fabrication and cost requirements of mass production;

(f) to provide a fingerprint recording device with optical properties which facilitate scanning of the fingerprint image into an automatic fingerprint identification system (AFIS).

These and other objects are accomplished in accordance with the present invention by coating, treating, or impregnating an area of the document with reflective inks, paints, foils, or other fingerprint sensitive materials. Over this prepared area a protective cover is hingedly mounted to protect the prepared surface from premature impressions until such time as a latent fingerprint is applied to the document. At such time, the protective cover may be lifted to expose the prepared surface so that it may be touched by a finger which deposits on this prepared surface a latent fingerprint image. The cover may then be replaced over the fingerprinted area to protect the latent fingerprint image from alteration or adulteration. This fingerprint pad is intimately and permanently a part of the document and serves as a means of positive identification should the identity of the transacting party ever be called into question. Still further objects and advantages will become apparent from consideration of the ensuing description and drawings.

BRIEF DESCRIPTION OF DRAWINGS

In FIGS. 3 through 5 the cover is shown as being partially lifted from the document.

REFERENCE NUMERALS IN DRAWINGS

50—protective cover
52—tape hinge
54—adhesive hinge
56—creased lift tab
D—document, or base sheet material
F—latent fingerprint image
58—serrated lift tab
60—hold-down adhesive
62—fingerprint sensitive adhesive
64—image enhancing layer.

DETAILED DESCRIPTION OF PREFERRED EMBODIMENT

Figure 1:
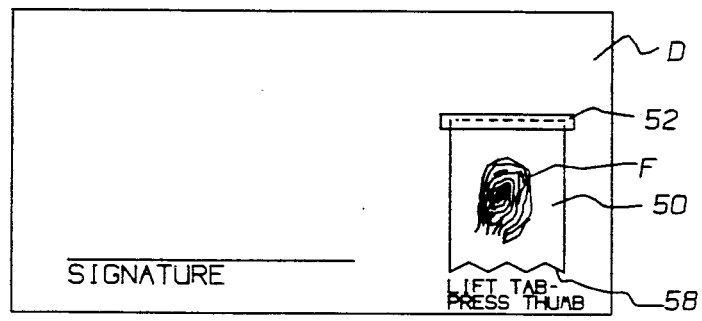
FIG. 1 is a top view of the document showing the fingerprint area with the hinged cover thereon.

As seen in FIG. 1, the fingerprint recording device is typically mounted on a base sheet material or document D in any convenient location. In this figure, the latent fingerprint image F is shown as being visible through the protective cover 50. A latent fingerprint image is herein defined as a naturally occurring fingerprint image which has not been artificially enhanced with inks, powders, chemicals or other substances which are deliberately applied to the finger.

The protective cover 50 is affixed at one end to the document by a tape hinge 52. Typically the protective cover 50 would be constructed of a flexible material such as plastic, mylar or cellophane. If viewing of the fingerprint image through the protective cover is desired, the protective cover may consist of a transparent, light polarizing material. In this case, the polarizing effect of the protective cover will reduce glare and provide for greater contrast and visibility of the fingerprint ridge detail.

The protective cover 50 may also be designed to incorporate a serrated lift tab 58 which is located on the side opposite to the hinge. Functionally, the serrated edges on tab 58 make it easier for the user to get an initial grip on the cover tab because the pointed tips of the serrated edge offer concentrated pressure points to a person's thumb which in turn makes it easier to gain an initial grip on the tab.

At the time of a transaction such as a purchase, the authorizing person signs the document and then grips the serrated lift tab 58 and lifts the protective cover 50 upwards, during which action the cover will pivot around its hinged point at 52. When the cover is lifted, the area of the document to receive the fingerprint is exposed. The authorizing person then imprints the exposed area with a fingerprint. The cover 50 is then pivoted back down over the latent fingerprint image F to protect the print from contamination or degradation. In the event that the identity of the authorizing person is ever questioned or challenged, the cover 50 can be easily removed to allow for unobstructed processing of the fingerprint by forensic experts. Since the cover may be repeatedly removed without damaging the fingerprint image, the image may be processed with any number of techniques in addition to standard photographic enlargements. Such techniques might include superglue image enhancing or chemical bonding of image enhancers to the latent fingerprint image.

Figure 2:
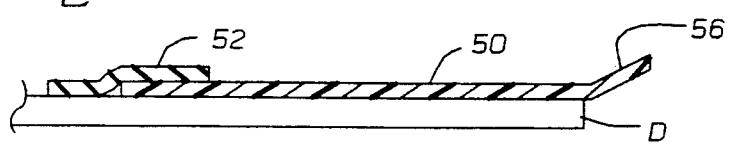
FIG. 2 through 5 are side sectional views of the fingerprint protection device showing different configurations for attaching the cover to the document, different lift tabs for the cover, and different mechanisms for holding the cover down in place.

An alternative tab design is shown in FIG. 2, wherein a creased lift tab 56 is shown in a side sectional view. In this embodiment the tab portion of the cover is formed to provide a permanent upward crease. This crease lifts the edge of the tab above the plane of the document's surface, making it easier to find and grasp the tab's edge. This action may be further enhanced by positioning the tab to extend slightly beyond the document's edge. The features of a creased tab and a serrated tab could obviously be combined into a single design wherein the tab edge of the protective cover is cut with a serrated edge and also creased upward.

Figure 3:
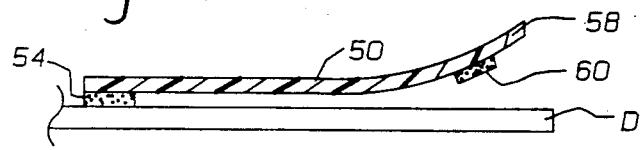

FIG. 3 illustrates a side sectional view of another embodiment of this invention wherein the tape hinge 52 is functionally replaced by an adhesive hinge 54. The adhesive hinge 54 possesses strong bonding qualities to both the document and the protective cover 50 so that the cover may not become accidentally separated from the document.

FIG. 3 also shows the optional use of a hold-down adhesive 60 which is typically an adhesive-like material. The hold-down adhesive 60 is used to hold the protective cover down in place so that it does not flap freely during the handling of the document. This same function can alternatively be achieved by using a material for the protective cover which is stiff enough that, in combination with the hinge, it naturally tends to hold itself into a closed position as shown in FIG. 2 wherein a hold-down adhesive is not necessary.

In FIG. 3 the hold-down adhesive 60 is shown as being strongly adhered to the protective cover 50 which is partially lifted. In this embodiment, the hold-down adhesive has only a weak, tacky attraction to the document and but a strong attraction to the cover and so will always follow the cover whenever the cover is lifted. The qualities of this type of adhesive are seen in the popular "Post-it Notes" which have a selectively bonding adhesive stripe which allow sheets of this notepaper to be temporarily attached to a document and yet the weak attraction of the adhesive to the document allows the note sheet to be removed from the document without leaving behind unwanted adhesive marks.

Figure 4:
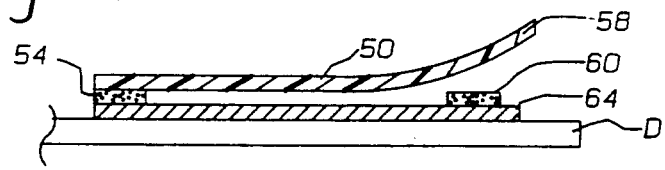

The embodiment shown in FIG. 4 is the similar to the variation shown in FIG. 3 except that the hold-down adhesive 60 in this case has a strong adherence for the document but only a weak adherence to the protective cover. In this embodiment, when the cover is lifted, the hold-down adhesive always remains with the document.

In FIGS. 2 and 3 the document itself is the imprinting material upon which the latent fingerprint image F is captured and preserved. In FIG. 4, however, the fingerprint image F is applied to an optional image enhancing layer 64.

The image enhancing layer 64 is a reflective or tinted material which serves as a background for the fingerprint to optically highlight the fingerprint image, making viewing, photographing, and processing of the fingerprint easier. This image enhancing layer is irremovably incorporated into the document by either printing the area with an ink, screening the area with a paint, or pressure stamping the area with a foil. If a reflective or metallic ink, paint, or foil is used, this reflective background will produce a mirror-like effect which will produce a distinct shadowing effect of the fingerprint ridge patterns, whereby the fingerprint image will become more highly visible to the naked eye.

Other means of incorporating an image enhancing layer into the document would naturally follow from this disclosure. For example, it is conceivable that the document itself may be made up of three layers, using, for example, a reflective mylar sheet sandwiched between two layers of paper. With such document material, the top layer of paper could be scored and stripped off in the designated fingerprinting area to expose the reflective material only in that area of the document. The hingedly mounted protective cover would then be mounted over the exposed reflective surface.

Figure 5:
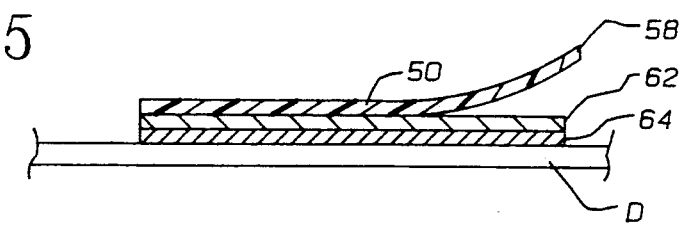

FIG. 5 illustrates the use of a second optional layer of fingerprint sensitive imprinting material 62 which may be incorporated directly onto the surface of an image enhancing layer 64, or alternatively, if an image enhancing layer is not used, onto the surface of the document.

As in the case of the hold-down adhesive 60, the fingerprint sensitive imprinting material 62 has a strong adherence for the document but only a weak adherence to the protective cover 50. The fingerprint sensitive imprinting material 62 can be screened or painted onto the document. Alternatively, the protective cover itself can be used as a carrier for the imprinting material which is transferred to the document when the cover is set into place.

The fingerprint sensitive imprinting material 62 is typically a transparent or semi-transparent, tacky substance which accepts the imprint of the finger. The use of a tacky substance for the imprinting material 62 serves several purposes. First, a tacky surfaced imprinting material 62 more effectively captures the moisture and contaminants which exist in a naturally occuring fingerprint. Second, a tacky surfaced imprinting material 62 also serves to reduce the possibility of smudging a latent fingerprint image due to movement of the finger since the finger tends to pull away from the tacky surface rather than smear across the surface. Third, a number of applications exist in which the fingerprint image is to be immediately processed, photographed, or digitized, and there is little or no need to hinge the protective cover 50 back into its original position. In these applications, a hinging means for the protective cover 50 may be omitted, as shown in FIG. 5, since the tacky surface of the fingerprint imprinting material 62 would itself be sufficient to hold the protective cover in place until a fingerprint is about to be recorded. Fourth, in applications where a hinged cover is required, such as a tape-hinge 52, the adhesive-like, tacky surface of the imprinting material 62 would also serve to provide the functions of the hold-down adhesive 60 in FIG. 4.

In addition, the fingerprint sensitive imprinting material may be treated to enhance the visibility of the fingerprint image which it captures. For example, the fingerprint sensitive imprinting material 62 may be impregnated with reagents which will change color after coming into contact with the salts, water, oils, dead skin, or other materials such as "sebum," a fatty substance secreted by the sebaceous glands, contained in a naturally occurring latent fingerprint. A number of such reagents are already in wide use for the processing of latent fingerprints. For example, a number of organic dyes such as "berberin" and "diazine" will react with the sebum in a latent fingerprint causing it to fluoresce in ultra-violet light. By impregnating an adhesive-like layer of imprinting material 62 with one or more of these reagents, the fingerprint image will "develop" on the surface of the imprinting material making the image more visible for immediate processing or digital scanning. Furthermore, since the imprinting material has a dense, adhesive-like, non-porous nature, the image will not tend blur over time due to migration of the imaging material away from the reaction site, which is a common problem in most two chemical fingerprinting methods.

As new materials are developed, it may be possible to incorporate the functions of an image enhancing layer 64 and the fingerprint sensitive imprinting material 62 into a single layer of fingerprint receptive material which would both capture the latent fingerprint image and optically highlight its features. Alternatively, in some applications, only one of the optional layers, 62 or 64, would be employed.

RAMIFICATIONS AND SCOPE OF INVENTION

It should be noted that this invention offers considerable advantages over the prior art in that it easier to fabricate in a mass production process and employs a minimal number of parts. In its simplest form, such as shown in FIG. 2, for example, the invention involves only two parts which simple "pick-and-place" equipment may place on a document.

Similarly, the embodiments shown in FIGS. 3 and 4 can be constructed by using the protective cover 50 as the carrier for the adhesive hinge 54 and hold-down adhesive 60. In these cases, the adhesive would be screened onto rolls of the protective cover material. During the fabrication of the documents, fabrication machinery would automatically cut rolls of the cover material to size and press it into position on the document, completing the fabrication in one step. Similarly, the embodiment shown in FIG. 5 can be achieved by printing, screening, or stamping of the image enhancing layer 64 and fingerprint sensitive imprinting material directly onto the document.

Thus, the conception of this invention carefully eliminates any powders or folds, and incorporates non-movable layers such as the imprinting material layer 62 and image enhancing layer 64 into the document itself, dramatically simplifying construction and reducing the overall cost as compared to the fingerprint pad devices envisioned in the prior art.

Numerous modifications of this device for other fingerprint identification tasks will be immediately obvious to those skilled in the art. For example, the device could be advantageously used as an inkless fingerprinting medium for use in automatic fingerprint identification system (AFIS) used by police departments, driver registration programs, or I-Search children identification programs. In these applications, the fingerprint is to be immediately processed and digitized, therefore, a hinged cover is not required.

An embodiment suitable for AFIS applications is shown in FIG. 5. In this case, the protective cover 50 is not hinged. The sole purpose of the protective cover 50 in this embodiment is simply to protect the fingerprint sensitive imprinting material 62 and the image enhancing layer 64 until the latent fingerprint image is about to be taken. After the protective cover 50 is stripped away, the fingerprint is placed on the fingerprint sensitive imprinting material 62. The document D carrying the fingerprint recording device can then be immediately placed under a fingerprint processing camera to be photographed or digitized into a computer image.

The use of an image enhancing layer 64 which employs a mirror-like reflective surface is especially well suited to electronic scanning of a fingerprint image for AFIS applications. This is because the distinction between a reflective surface and a diffused surface can be easily detected with an electronic scanner.

To those familiar with the art, this invention could also be readily used as a substitute for fingerprint lifting tape. In this application, forensic technicians at a crime scene powder a latent print with a dark or light colored powder and then capture the powder image of the fingerprint onto a clear lifting tape which is then pressed onto a contrasting white or black evidence card. It is readily apparent that the present invention as shown in FIG. 5 could serve as a replacement for the lifting tape and evidence cards currently in use. In this application, the protective cover 50 would be lifted to expose the tacky surface of the fingerprint sensitive imprinting material 62 which would be pressed against the powdered latent fingerprint. The powder would adhere to the tacky surface to preserve and record the pattern of the fingerprint image. The protective cover 50 would be put back into place, and the powder image, no matter what its color, would be clearly visible against the mirror-like reflective background provided by the image enhancing layer 64.

CONCLUSION

Accordingly, the reader will see that the fingerprint recording device of this invention can be used to record a high quality latent fingerprint easily and conveniently, without soiling the user's fingers with inks or other foreign substances. In addition, this invention has a number of additional advantages in that it overcomes numerous obstacles to the mass production of an inkless fingerprinting system onto mass produced documents;

it eliminates the possibility of fraudulent transfer of a fingerprint image from one document to another by using the document itself as the base material for the fingerprint recording device;

it eliminates the use of waste sheet layers which must be discarded it provides for a protective cover which can be easily removed from the protected fingerprint image to allow for unobstructed forensic processing of the fingerprint image using any of a wide variety of techniques; and it provides a means to optically enhance a naturally occuring latent fingerprint through the use of a mirror-like reflective background.

Although the description above contains many specificities, these should not be construed as limiting the scope of the invention but as merely providing illustrations of some of the presently preferred embodiments of this invention. For example, the protective cover and image enhancing layer could be tinted to take advantage of special lighting conditions; the fingerprint recording area could be enlarged to encompass the entire document if the document is used for recording a full set of ten prints in a police station; the tab to the protective cover could consist of a separate material attached to the cover, etc.

Thus, the foregoing is considered as illustrative of the principles of the invention, but is not exhaustive. Numerous modifications and changes will be obvious to those skilled in the art, especially in the formulation of ingredients, materials used, and construction of the hinging mechanism and lift-tab. Therefore, it is not desired to limit the invention to the exact construction shown and described, and accordingly, all modifications and equivalents which may be resorted to fall within the scope of the invention.

I claim:

1. A latent fingerprint recording device, comprising;
   a sheet of material possessing a reflective surface of sufficient size to record at least one fingerprint image over said reflective surface; and
   a protective cover mounted above said reflective surface to protect the surface from contamination or adulteration during storage.

2. The fingerprint recording device of claim 1, further including a fingerprint sensitive material applied to said reflective surface to receive an imprint of the latent fingerprint images.

3. The fingerprint recording device of claim 2, wherein said fingerprint sensitive imprinting material is a material which is impregnated with chemical reagents which react to the materials contained in a naturally occurring latent fingerprint to produce a more visible image of the fingerprint image.

4. The fingerprint recording device of claim 1, further including a hinge means for preventing said protective cover from accidentally separating from said sheet of material.

5. The fingerprint recording device of claim 1, wherein said protective cover includes a tab means integral with said protective cover by which the cover may be more easily grasped and lifted.

6. The fingerprint recording device of claim 1, wherein said protective cover consists of a transparent, light polarizing material to increase the contrast and visibility of the fingerprint image when viewed through the cover.

7. A latent fingerprint recording device, comprising;

a document having a reserved area of sufficient size to record a naturally occurring fingerprint image over said document's surface;

a layer of image enhancing material which is printed, painted, screened, stamped, or impregnated into said reserved area of said document; and a protective cover hingedly mounted along an edge of said reserved area of said document to protect said image enhancing material from degradation or adulteration during storage, whereby said protective cover may be repeatedly lifted or replaced over said reserved area to allow for recording the fingerprint image and unobstructed processing of the fingerprint image.

8. The fingerprint recording device of claim 7, further including a layer of adhesive-like material applied between said document and said protective cover whereby said protective cover is prevented from accidentally lifting off of said document.

* * * * *